(12) United States Patent
Draper (10) Patent No.: US 7,689,318 B2
(45) Date of Patent: Mar. 30, 2010

(54) INVENTORY CONTROL AND PRESCRIPTION DISPENSING SYSTEM

(76) Inventor: Lonnie Draper, 565 Frank Shaw Rd., Tallahassee, FL (US) 32308

(*) Notice: Subject to any disclaimer, the term of this patent is extended or adjusted under 35 U.S.C. 154(b) by 603 days.

(21) Appl. No.: 11/507,093

(22) Filed: Aug. 18, 2006

(65) Prior Publication Data
US 2007/0043469 A1 Feb. 22, 2007

Related U.S. Application Data

(60) Provisional application No. 60/709,645, filed on Aug. 19, 2005.

(51) Int. Cl.
*G06F 17/00* (2006.01)
(52) U.S. Cl. ............... 700/236; 221/2; 221/82; 221/92; 221/93; 221/9; 700/243; 700/244
(58) Field of Classification Search .............. 221/2, 221/82, 92, 93, 9; 700/243, 244, 237
See application file for complete search history.

(56) References Cited

U.S. PATENT DOCUMENTS

| | | | |
|---|---|---|---|
| RE35,743 E * | 3/1998 | Pearson ................... 221/2 |
| 5,964,374 A * | 10/1999 | Yuyama et al. ............. 221/17 |
| 6,529,801 B1 | 3/2003 | Rosenblum |
| 6,697,704 B2 | 2/2004 | Rosenblum |
| 6,711,460 B1 * | 3/2004 | Reese ..................... 700/216 |
| 6,735,497 B2 * | 5/2004 | Wallace et al. ............ 700/231 |
| 6,766,218 B2 | 7/2004 | Rosenblum |
| 6,892,941 B2 | 5/2005 | Rosenblum |
| 7,137,528 B1 * | 11/2006 | Yates et al. ................ 221/82 |
| 7,471,993 B2 * | 12/2008 | Rosenblum ............... 700/237 |
| 2003/0088332 A1 | 5/2003 | Rosenblum |
| 2003/0093181 A1 | 5/2003 | Rosenblum |
| 2004/0164146 A1 | 8/2004 | Rosenblum |
| 2004/0215369 A1 | 10/2004 | Rosenblum |

* cited by examiner

*Primary Examiner*—Gene Crawford
*Assistant Examiner*—Timothy R Waggoner
(74) *Attorney, Agent, or Firm*—William H. Hollimon (57) ABSTRACT

An inventory control and prescription management and dispensing system including a dispensing vault for storing and dispensing prescriptions in communication with a central computer system which communicates with prescription providers, insurance companies and other third parties. The vault includes robotic means for dispensing pre-filled prescriptions with the aid of RFIDs, barcodes or other means for verifying the medication to be dispensed. The vault uses patient biometrics, a patient registration system, insurance information and doctor information to process the transaction and dispense a specifically labeled pre-filled prescription to the patient.

3 Claims, 12 Drawing Sheets

FIG. 12

INVENTORY CONTROL AND PRESCRIPTION DISPENSING SYSTEM

PRIORITY OF INVENTION

This application claims priority of invention under 35 USC 119(e) from U.S. Provisional Patent Application 60/709,645 filed Aug. 19, 2005.

TECHNICAL FIELD

The present invention concerns inventory control systems and dispensing systems for, in particular, prescription drugs.

BACKGROUND OF THE INVENTION

The number of prescriptions filled each year by pharmacies in the United States is fast increasing. This puts additional demands on pharmacies and pharmacists to fill prescriptions in a timely manner. Many people have experienced the frustration of a long wait at a pharmacy simply to have a common prescription filled or refilled.

There are numerous problems with the present system used for the dispensing of prescription medicines. First, current practices rely upon the memory of the prescription provider as to the pharmaceutical to be prescribed. This introduces a series of potential errors. Second, most prescriptions are produced without the aid of checking against a known database of allegories and interactions. Third, it primarily relies upon hand-written scripts that must be translated by a pharmacist. This injects a first level of translation error into the process, and often requires a pharmacist to verify a prescription with the prescribing doctor. This adds additional time and delay to the prescription filling process. Fourth, it requires patients to obtain scripts from their doctors and then travel to their pharmacy to have the prescription filled. Once at the pharmacy, patients may be subjected to delays and human error caused by pharmacists rushing to meet the accumulated demand.

Various attempts have been made to automate the dispensing of prescription drugs to address these issues. However, these attempts suffer from one or more of the following shortcomings. First, a critical concern in any remote dispensing situation (i.e., one where the dispensing is not under the direct control of a pharmacist) is that only an authorized person receive the medication and that the corresponding method of authorization should not be readily forged or compromised. Thus, a secure method of patient identification is required. These known systems typically generate a code at the time a prescription is generated. This code is then entered into a remote dispensing apparatus by a person desiring to obtain a prescription. However, this code is easily transferred to, or otherwise obtained by, persons who are not authorized to obtain the prescription. Further, most patients will record the code on a document rather than risk forgetting the code. This provides another mechanism by which an authorization code can be obtained by an unauthorized user. Thus, these known systems lack such a secure method of patient identification and introduce multiple points for such a code to be lost or otherwise compromised.

Second, because a pharmacist need not be present in remote dispensing situations, a remote dispenser must include multiple, redundant verifications to ensure that the prescribed medication, and only the prescribed medication is, in fact, dispensed. Known remote dispensing systems typically employ a single level of verification that is typically comprised of a barcode scan of a barcode that was applied by a repackaging pharmacy prior to loading of the product into inventory of the remote dispenser. If a product is mislabeled at the repackaging pharmacy, a single level of verification will not determine that the product is mislabeled, greatly increasing the possibility that an incorrect product is dispensed. Likewise, if a product package is improperly filled (quantity too high or too low), these known systems have no ability to determine this condition. Thus, there is a need for a remote dispensing system that provides multiple, redundant verifications to ensure that only the correct prescription is dispensed.

Third, the present systems lack coordination between the upstream pharmaceutical suppliers and the remote dispensing devices, such that an excessive amount of time and labor is required to restock the dispenser and verify that stocked drugs have not reached an expiration date, or have otherwise had their quality compromised (e.g., through a temperature transient).

Fourth, the present systems lack a secure method of transferring prescription medications from a repackaging pharmacy to a remote dispensing device and from a remote dispensing device to repackaging pharmacies.

Fifth, the known systems do not provide for a high density of product storage and the ability to randomly access any product contained in the inventory of the remote dispensing device. As a result, the frequency of need for human interaction to restock a remote dispenser is increased. Further, this lack of random access significantly limits the number of different products that can be stocked in a remote dispenser.

Accordingly, there is a need for an inventory control and prescription dispensing system that quickly and efficiently delivers prescription drugs to patients in locations where a pharmacist is not necessarily physically present, that minimizes the potential for translation errors between a prescriber and a pharmacist, that provides adequate security that prescription drugs are only dispensed to authorized persons, that provides multiple, redundant systems to ensure that correct prescription drugs are dispensed, that coordinates the restocking and quality control of prescription drugs available within the remote dispenser, that provides for a secure method of transporting prescription medications between a repackaging pharmacy and a remote dispensing device, and that provides for high density product storage and random access to products stored.

SUMMARY OF THE INVENTION

To address these needs, the inventor has devised a new system and method for prescribing, dispensing, managing inventory, and ensuring the integrity and security of dispensed medications. One embodiment consists of a dispensing system that is self contained and stores a variety of commonly filled prescription drugs. This dispensing system is in communication with prescribing providers, insurance companies, banks and credit card companies, pharmacist, pharmacy business management systems, point of sale systems, repackaging pharmacies, and patients. This system allows for the remote dispensing of prescription medications, while maintaining the security and integrity of the medications, maintaining control over to whom products are dispensed, allowing for communications between the patient and a remote or local pharmacist, and facilitating insurance and financial transactions. The system further provides for increased storage density and random access capabilities that allow any individual product within the remote dispenser to be accessed at any time.

DESCRIPTION OF THE PREFERRED EMBODIMENTS

The following detailed description, which references and incorporates the Figures, describes and illustrates one or more specific embodiments of the invention. These embodiments are offered not to limit but only to exemplify and teach the invention, and are shown and described in sufficient detail to enable those skilled in the art to practice the invention. Thus, where appropriate to avoid obscuring the invention, the description may omit certain information known to those skilled in the art.

The inventory control and prescription management and dispensing system of the present invention provides for the safe, secure, and convenient dispensing of prescription medications in a variety of nontraditional settings, while providing safeguards to ensure that the proper medication is dispensed to the proper person, and that the quality and efficacy of the medication has been preserved and maintained. It provides a secure system for transferring prescription medications between repackaging pharmacies and remote dispensing devices. It further provides the flexibility to accommodate a variety of transaction types and permutations.

System Overview

Figure 1:
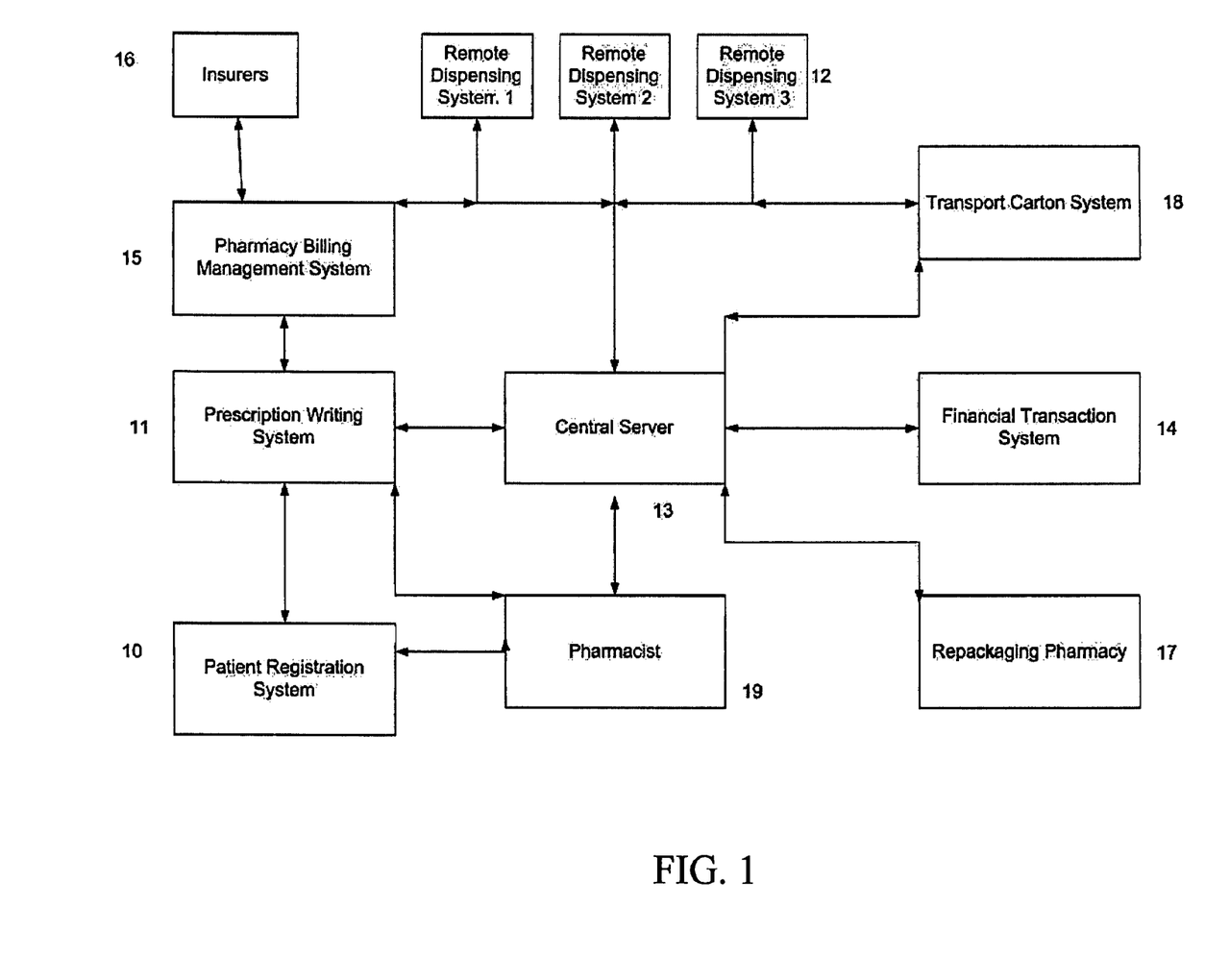
FIG. 1 is a block diagram of an embodiment of the present invention.

Referring to FIG. 1, a block diagram of the inventory control and prescription dispensing system is shown. This system includes the Patient Registration System (PRS) 10, the Prescription Writing System (PWS) 11, the Remote Dispensing System (RDS) 12, the Central Server 13, the Financial Transaction System (FTS) 14, the Pharmacy Billing Manager System (PBMS) 15, associated Insurers 16, Repackaging Pharmacy 17, Transport Carton 18, and pharmacists 19. A communications network allows for communications between the various components. Proprietary software controls security and permissions for communications, and access to stored data throughout the system.

Patient Registration System (PRS)

PRS 10 is the point at which essential patient information necessary to facilitate the use of RDS 12 is captured. This information includes the patient's personal data, including name, date of birth, demographic information, insurance information, financial (bank and/or credit card information) and physician name. A patient's medical history including allergies, problem lists, current prescriptions and the like, are also captured. Biometric information is collected by the PRS and may include fingerprint, iris scan, voice scan, photographic scan, or other biometric information that is unique to a particular patient. This biometric information provides a unique identifier for each patient and is used to verify patient identity at RDS 12. Information that is collected through PRS 10 may be stored on a local RDS 12 and/or stored on central server 13. PRS 10, via a communications network, communicates primarily with RDS 12, other registration systems, prescription writing system 11, and central server 13.

Prescription Writing System

PWS 11 allows a prescription provider to generate either an electronic or paper based script. PWS 11 includes a handheld computer (commonly referred to as a PDA) that is networked to RDS 12, typically through a server located in the provider's office. This communication may be either through a wired network or a wireless network. Proprietary software is used to handle data transfer and communications between PWS 11 and RDS 12, central server 13, and PRS 10. As a first step, patient specific information, such as demographics, insurance information, medical history, problem list, allergies, and current medications that is collected by PRS 10 is transmitted to the PWS 11. RDS 12 transmits a current inventory of products (a formulary) to PWS 11. Following a patient encounter, a prescription provider desiring to write a prescription, enters the prescription into the PDA. The proprietary PWS software then performs a drug utilization review, which includes drug-drug interaction, dosage range checking, patient allergy checking, pregnancy and lactation alerts, and other safety checks. The PWS software, through PBMS 15, also determines whether the prescribed medication is covered by the patient's insurance 16 and is available at RDS 12.

Any RDS 12 on the network can be queried to determine the availability of the prescribed medication. If the prescribed medication is not available through an RDS 12, or if the patient would prefer a paper based prescription, a paper based script can be generated through PWS 11. Otherwise, an electronic prescription is transmitted by PWS 11 to a RDS 12 that is specified by the patient or is transferred to a traditional pharmacy as an electronic prescription or by facsimile.

Remote Dispensing System

Vault System

Figure 3:
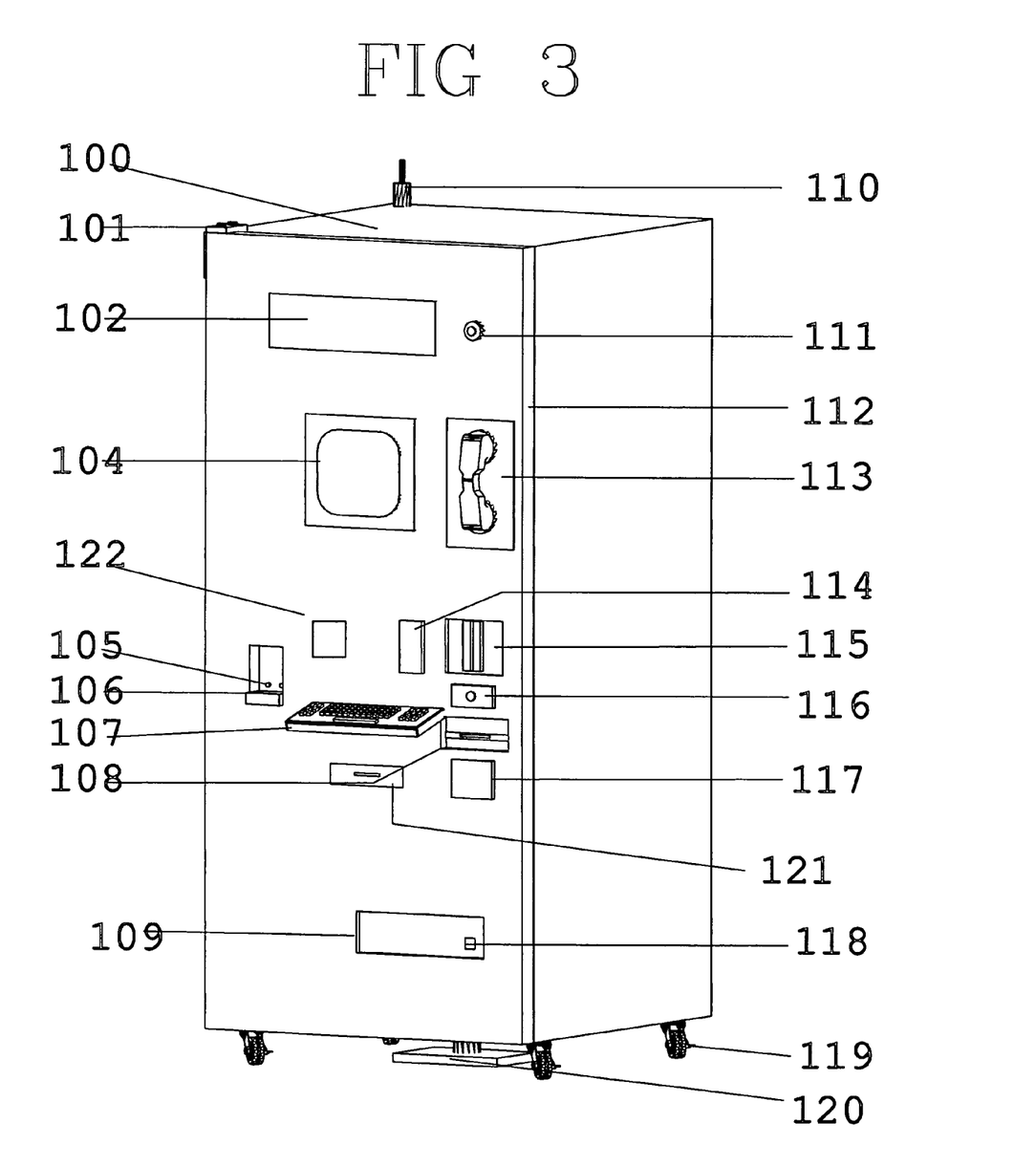
FIG. 3 is a front isometric view of an embodiment of the remote dispenser of the present invention.

Referring to FIG. 3, a front isometric view of RDS 12 is shown. RDS 12 consists of vault 100 in which products (not shown) are stored for dispensing. Vault door 112 is hingedly connected to vault 100 by hinges 101 and is secured in a closed position by lock 116. Positioned on or through vault door 112 are light 102 which provides illumination for the front of vault 100, camera 111, which captures a video record of transactions, video monitor 104 which provides user feedback, keyboard 107 for user data input, dispensing slot 106, through which product is delivered to users, pick-up sensor 105, which provides a signal when dispensed product is removed from dispensing slot 106, insurance card reader 108, which creates a bitmap image of a user's insurance card, loading door 109, through which product is introduced into vault 100 inventory, wireless antennae 110, for wireless communications, biometric reader 114, for capturing a user's biometric identification information, magnetic card reader 115 for capturing information contained on magnetic strips, such as credit cards, prescription reader 117, for creating bitmap images of paper scripts, printer 121, for printing receipts and product safety information, RFID sensor 118, for receiving communications from a transport carton (not shown) being placed into inventory, castors 129, for movement of vault 100, and tilt security device and sensor 120 for preventing movement of vault 100 and determining if vault 100 is being shaken, overturned, or otherwise disturbed.

Figure 4:
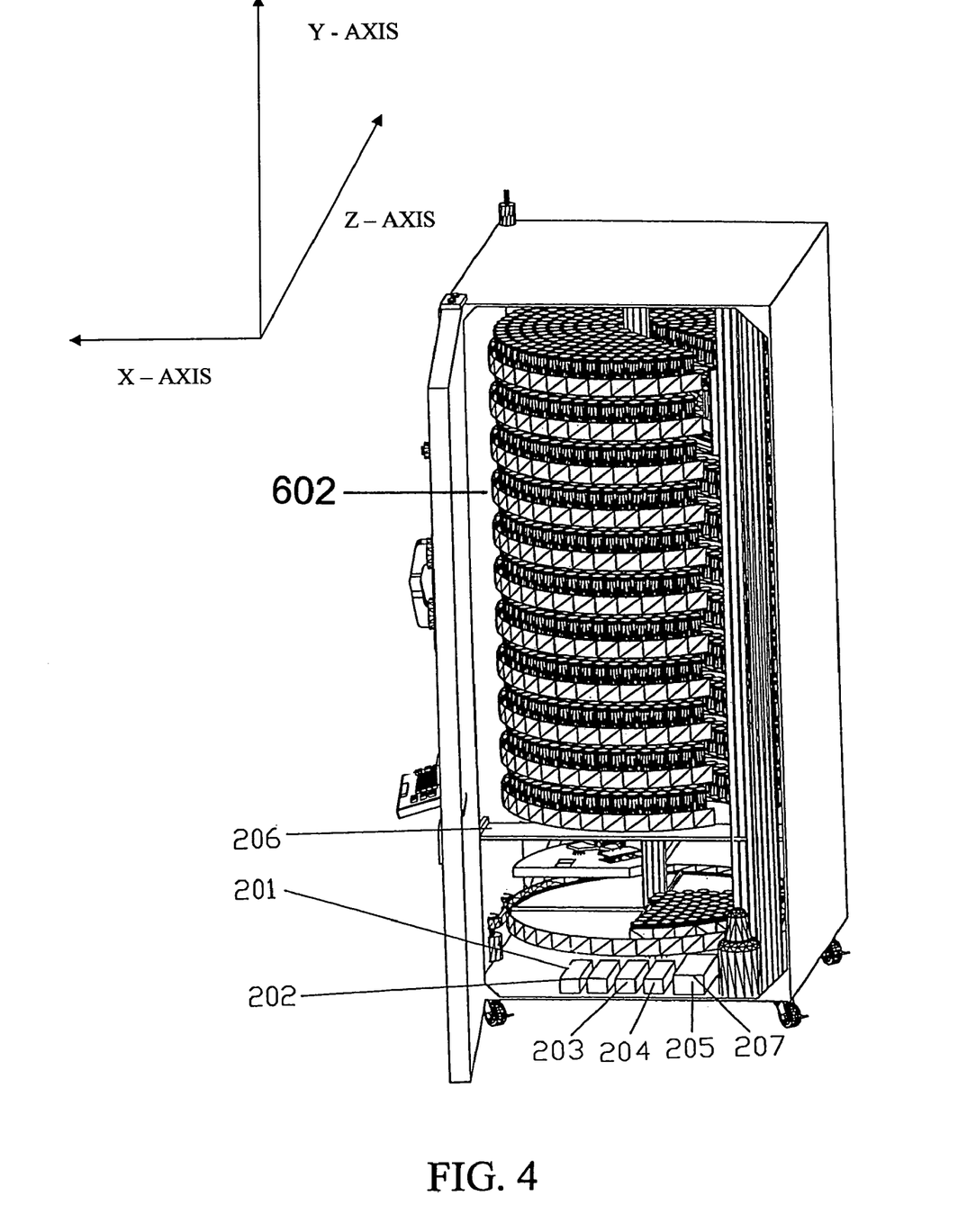
FIG. 4 is a front isometric view of the interior of an embodiment of the remote dispenser of the present invention.

Referring to FIG. 4, a front isometric view of RDS 12 is shown with vault door 112 in the open position. Security bar 206 provides a physical barrier between the lower portion of vault 100, where product is received through loading door 109 for placement into inventory, and the upper portion of vault 100 where product is stored for dispensing. Alternatively, security bar 206 may be formed as a plate that extends horizontally from the front of vault 100 to the rear of vault 100. Positioned in the base of vault 100 are battery backup 201, motor controller 202, refrigeration unit 203, communications module 204, and CPU 205 which also provides a memory for data storage. Shelf axel 904 extends vertically from the base of vault 100 to the top of vault 100. Rotating shelves 602 are rotatable about shelf axel 904 and are stacked vertically within vault 100.

Shelve System

Figures 5, 5A:
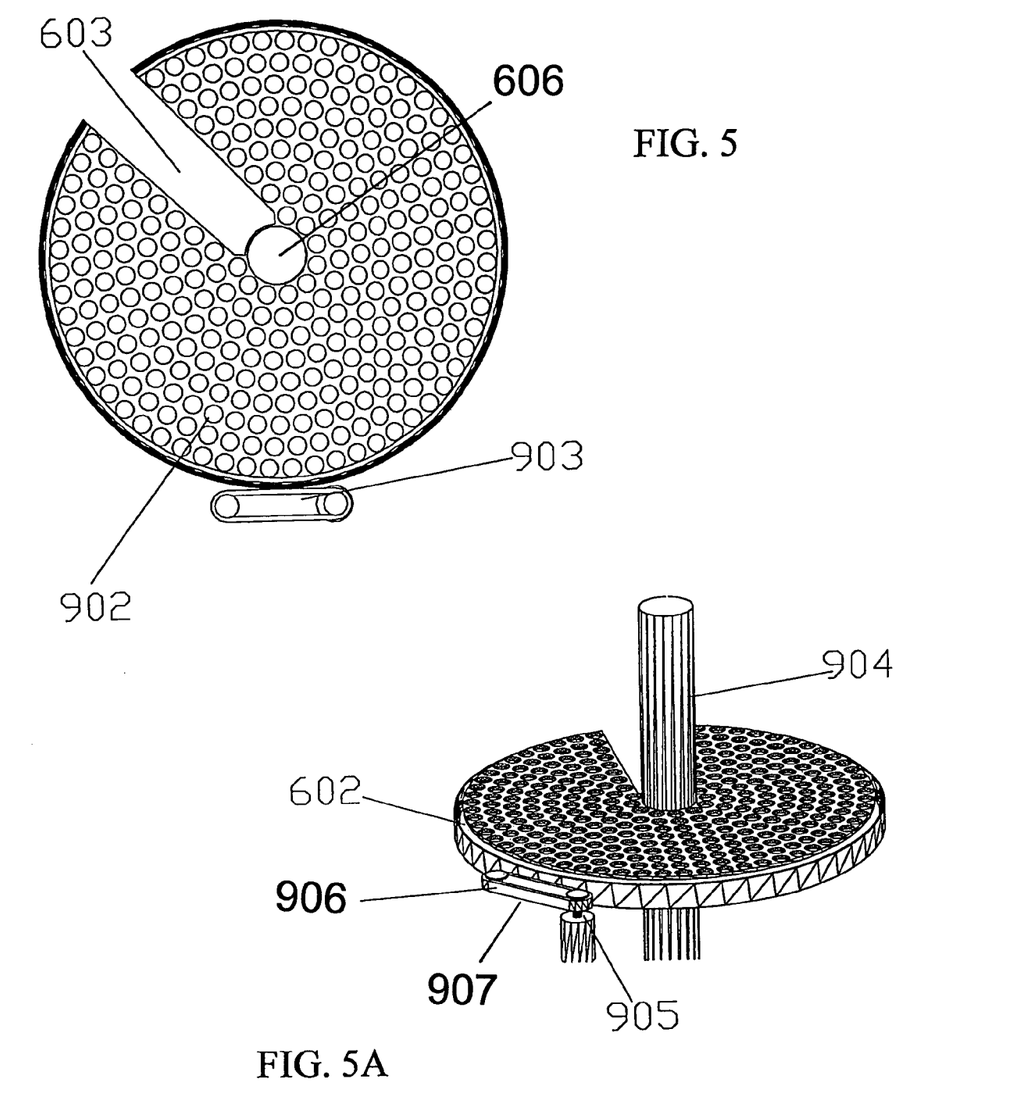
FIG. 5 is a plan view of an embodiment of the rotating shelve of the present invention.
FIG. 5A is an isometric view of an embodiment of the rotating shelve of the present invention.

As shown in FIGS. 4, 5, and 5A, in this embodiment rotating shelve 602 is substantially circular and may be formed from sheet metal or molded from a suitable plastic material. Shelve lip 608 defines the outer periphery of rotating shelve 602. Access slot 603 extends from central bore 606 to the periphery of rotating shelf 602.

Shelf lip 608 extends parallel to the axis of rotation of rotating shelve 602 from the periphery of rotating shelf 602, including the periphery created by access slot 603, and creates an axially extending shoulder which, in conjunction with shelf floor 607 defines a receiving space for storing product. Bottle holder insert 902 is positioned within this receiving space and includes a plurality of circular voids that are sized to accommodate standard sized prescription medicine containers.

Figure 6:
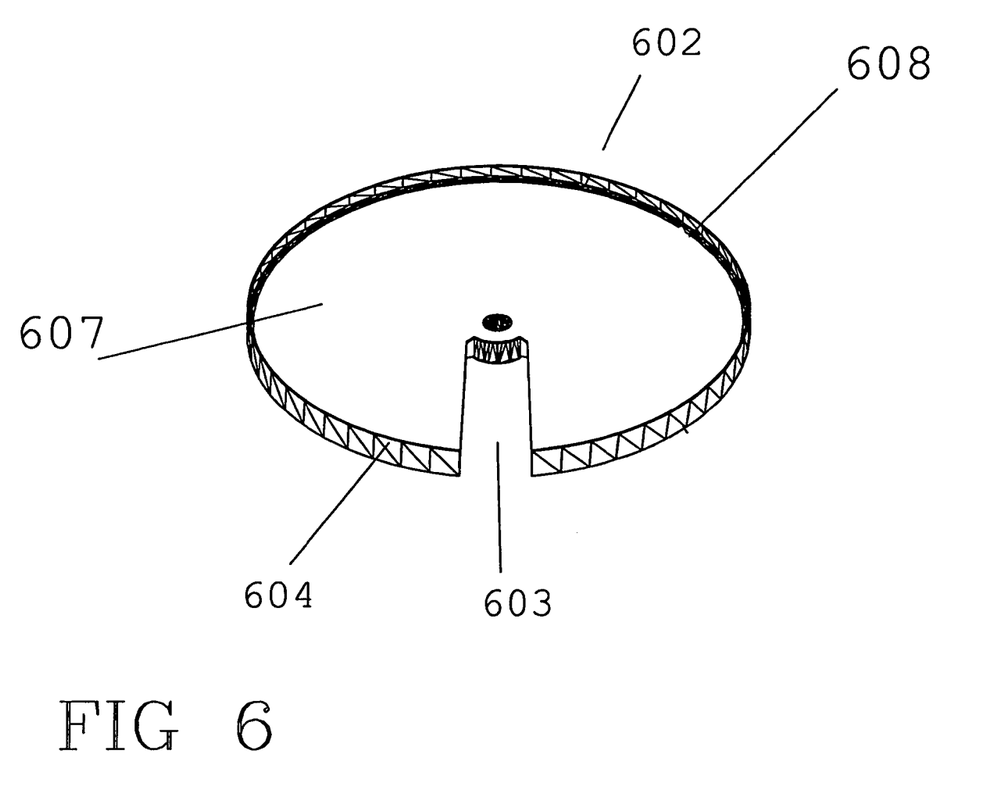
FIG. 6 is an isometric view of an embodiment of the rotating shelve of the present invention.

Rotation of rotating shelves 602 is performed by drive system 903. Drive system 903 consists of shelf drive motor 905, pulley 906, and drive belt 907. Each rotating shelve 602 is rotated by an individual drive system 903 (not shown for clarity). The distance between drive motor 905 and pulley 906 is slightly wider than the width of slot 603 so that rotation of rotating shelves 602 is effected even when drive motor 905 or pulley 906 is aligned with slot 603. Rotation of drive belt 907 results in a corresponding rotation of rotating shelf 602 about an axis defined by shelf axel 904. In one embodiment of the system rotating shelves 602 have surface mounted encoding strips 604 positioned along the outside surface of shelve lip 605. These encoding strips 604 are read by an encoder that is integrated into drive system 903 to allow the controlling software to detect and adjust the exact rotational position of each rotating shelve 602. Alternatively, or in conjunction with this method, an optical or magnetic encoder may be placed on each drive system 903 in order to detect rotating shelve 602 rotational position or adjust rotating shelve 602 rotational position. These forms of encoders typically allow for rotational position determination within an accuracy of hundredths of a millimeter.

In an alternative embodiment, shelves 602 are square or rectangular and do not rotate. In this embodiment, shelves 602 are supported from the perimeter of shelves 602 by engaging adjustable racks located within vault 100.

Robotic Arm System

Figure 2:
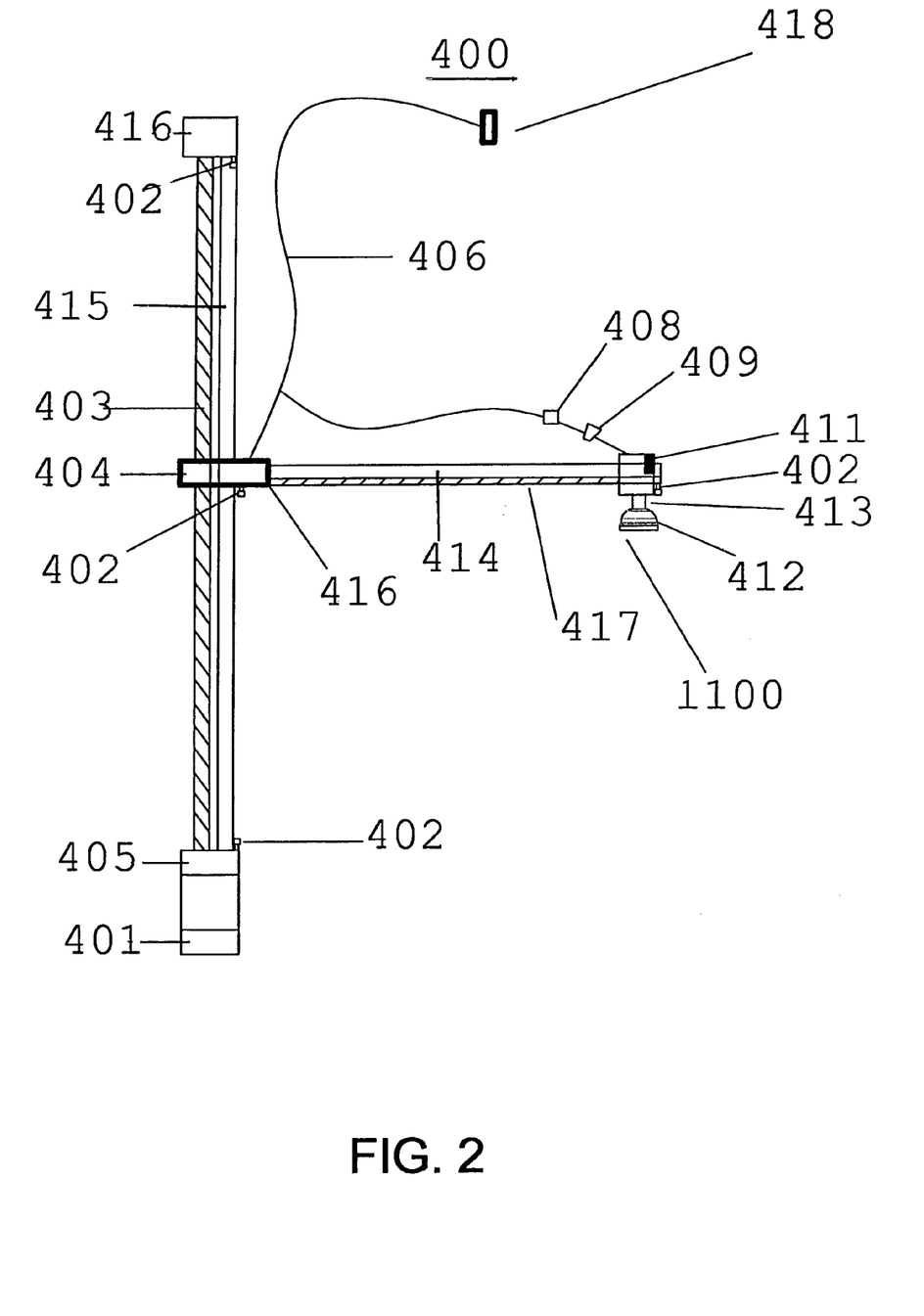
FIG. 2 is a side view of an embodiment of the robotic arm system of the present invention.

Referring to FIG. 2, robotic arm system 400 is shown. Robotic arm system 400 is located interior to vault 100 and extends vertically from the base of vault 100 to the top of vault 100 and is positioned to be proximate to the periphery of rotating shelves 602. Robotic arm system 400 is capable of vertical, horizontal, and depth movement. Vertical arm 415 extends between head support 416 which is attached to the interior ceiling of the vault and base support 401 which is secured to the floor of vault 100. Because of the need for security in this application all mounting hardware for the vertical axis is secured internally without obviously removable supports. Proximate to vertical arm 415, and also extending vertically between head support 416 and base support 401 is vertical lift screw 403. Vertical carriage 404 rides along vertical arm 415 and is driven vertically (Y-Axis) by vertical lift screw 403. This is accomplished by a engagement system commonly referred to as a ball screw or lead screw. In this embodiment of robotic arm system 400 the lift screw 403 moves through a threaded block attached to the vertical carriage 404. During rotational movement of lift screw 403 the rotationally fixed block is forced upward or downward according to the rotational direction of lift screw 403. Vertical drive system 405 includes a motor, gearbox, and position encoder, and provides the motive force to turn vertical lift screw 403 to effect movement of vertical carriage 404. The included encoder utilizes a magnetic or optical pick-up to count fractions of revolutions of vertical lift screw 403, from which the vertical position (Y-Axis) of vertical carriage 404 is determined. Limit switches 402 limit the travel of vertical carriage 404 in both upward and downward directions in a known manner and allow for further calibration and control of the system.

Horizontal drive system 416 includes a motor, gearbox, and position encoder, and provides the motive force to turn horizontal drive screw 417 to effect horizontal movement of grabber assembly 1100. Referring to FIG. 4, the width of vault 100 is defined to correspond to the X-axis, the depth is defined to correspond to the Z-axis, and the height is defined to correspond to the Y-axis. Grabber assembly 1100 moves along the length of horizontal arm 414 in a plane defined by the X and Z axes. The included encoder utilizes an optical or magnetic pick-up to count fractions of revolutions of horizontal drive screw 414, from which the position (location) of grabber assembly 1100 is determined with respect to the X and Z axes. Total travel of grabber assembly 1100 is limited, in a known manner, by limit switches 402, positioned proximate to each end of horizontal arm 414. In one embodiment, vacuum to grabber assembly 1100 is provided by vacuum pump 418 through vacuum line 406. Vacuum is controlled by suction sensor 409 and suction control solenoid 408. In another embodiment, suction and suction control are provided on grabber assembly 1100.

Figure 8:
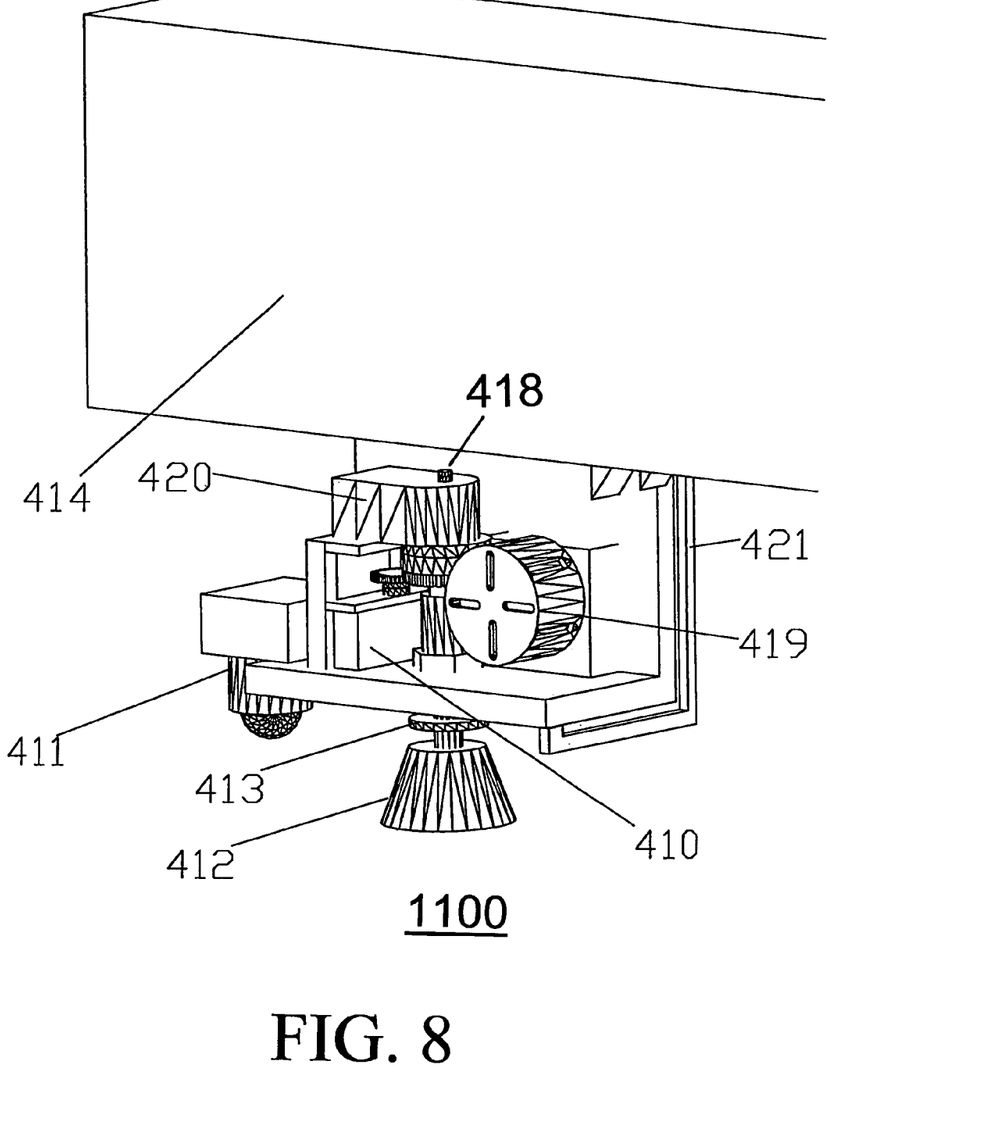
FIG. 8 is an isometric view of an embodiment of the grabber assembly of the present invention.

Referring to FIG. 8, grabber assembly 1100 is shown. Grabber assembly 1100 is composed of rotational motor 410, video/still camera 411, grabber/suction fitting 412, vertical position sensor 413, vacuum 419, optical encoder 420 and bracket 421. Bracket 421 is L-shaped with the vertical portion engaging horizontal arm 414 in a manner that allows for limited, damped vertical movement of bracket 421 with respect to horizontal arm 414. Grabber suction 412 is positioned below the horizontal portion of bracket 421 and is rotatable about an axis defined by shaft 418. In this embodiment, suction is supplied to grabber suction 412 by vacuum pump 419. Rotative motor 410 provides the motive force to rotate grabber suction 412. Optical encoder 420 determines the rotational position of shaft 418. Vertical position sensor 413 is used to determine the vertical (y-axis) position of grabber suction 412. Grabber video 411 provides a video image of the position and location of grabber assembly 1100 and a video image of product captured by grabber suction 412.

The combination of linear movement of grabber assembly 1100 and rotational movement of rotating shelves 602 provides complete random access capabilities to all product stored in the RDS vault. This allows for both high density storage and a wide product mix when compared to prior art systems.

Communications and Controls

The RDS utilizes an internal computer (processor, data storage, communications) 205 to manage and control the loading, inventorying, and dispensing of product. As shown in FIG. 1, the RDS 12 is also in communication with prescribing providers (through prescription writing system 11), patient registration system 10, repackaging pharmacies 17, pharmacy business management companies 15, insurance companies 16, financial institutions 14, and participating pharmacists 19. These communications are either internet based using secure internet protocols or local using proprietary or standard protocols and may be effected either through wired, or wireless, connections.

Several software applications are resident on the RDS computer 205. These applications control the receipt, loading, and verification of product placed into the RDS vault 100; management of inventory in the RDS vault 100; internal operations associated with the selection, retrieval, inventory and dispensing of product; product verification prior to dispensing; product labeling prior to dispensing; database functions; communications between the RDS and prescribing providers, patient registration systems, repackaging pharmacies, insurance companies, and banks and credit card companies; security and surveillance; patient identification; paper prescription reading; insurance card reading, product instruction printing; user interfaces.

Transport Carton System

Figure 12:
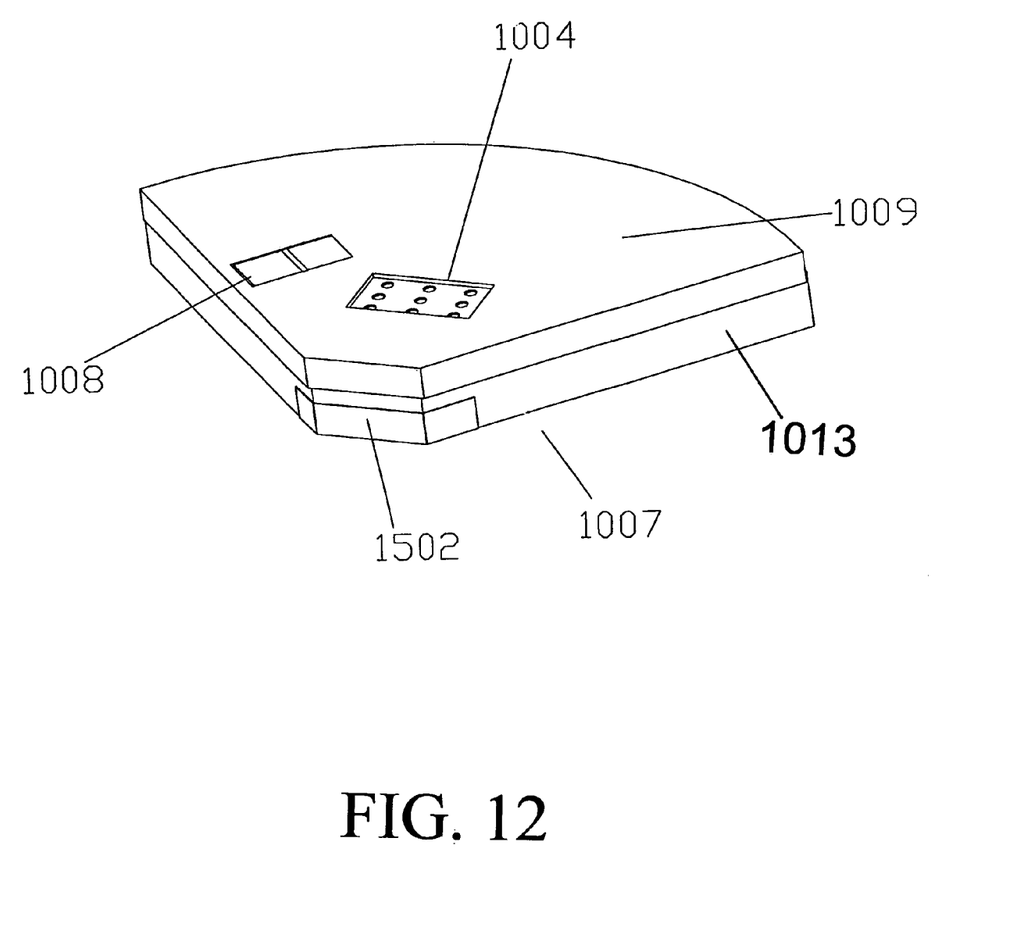
FIG. 12 is an isometrice view of an embodiment of the transport container of the present invention.

Referring to FIG. 12, transport carton 1007 is shown. Transport carton 1007 is used to securely transfer prescription medications to and from a repackaging pharmacy. In the embodiment shown, transport carton 1007 has an arcuate outer edge, spanning an arc of approximately 90 degrees, and two, perpendicular inner edges, extending linearly from each end of the arc. In this embodiment, transport carton 1007 is essentially shaped like a slice of pie that forms a 90 degree wedge. Transport carton lid 1009 is removably attachable to transport carton base 1013. Data/power port 1004 and shipping label 1008 are recessed into transport carton lid 1009. Alignment guide 1502 facilitates alignment of transport carton 1007 in vault 100. Data port 1004 includes a plurality of configurable contacts through which data is communicated and power is supplied. Transport carton 1007 is preferably fabricated from aluminum, structural plastic, or other similar material.

Figure 10:
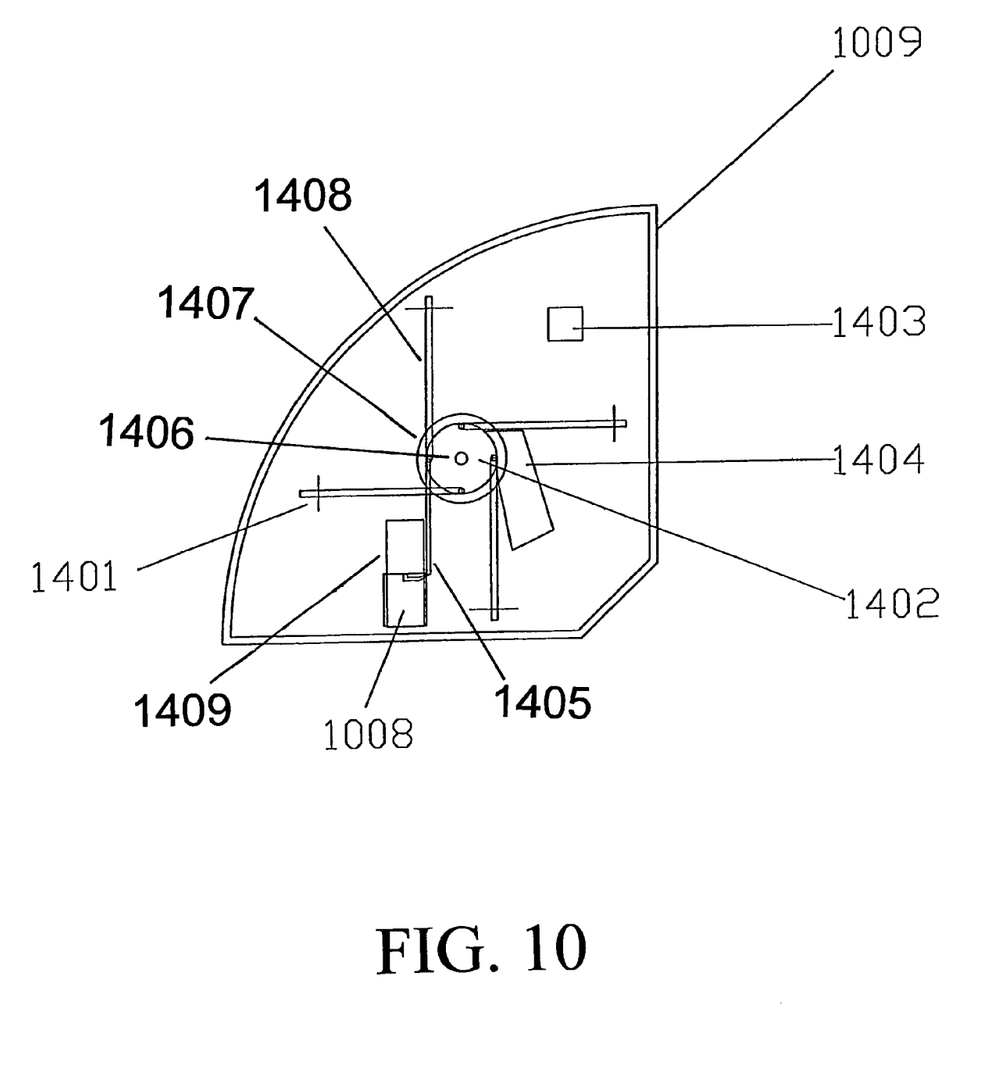
FIG. 10 is a plan view of an embodiment of the transport container lid of the present invention.

Referring to FIG. 10, an underside view of transport carton lid 1009 is shown. In this embodiment, locking mechanism 1402 includes a circular lock ring 1407, which is rotatable about lock axis 1406 and is driven by drive motor 1404. Four lock arms 1408 are pivotally attached to lock ring 1407 and equally spaced about the inner circumference of lock ring 1407. Lock guides 1401 are attached to the underside of transport carton lid 1009 and include a through bore for slidingly receiving the distal end of each lock arm 1408. Clockwise rotation of lock ring 1407 by drive motor 1404 extends each lock arm 1408 and engages the distal end of each lock arm 1408 with lock arm receiver 1501 (not shown) which is attached to transport carton base 1013. Reversing drive motor 1404 results in counter clockwise rotation of lock ring 1407 and the withdrawal of lock arms 1408 from sliding lock receivers 1501. Shipping label actuator 1405 is attached at a first end to lock ring 1407 and at a second end to slide 1409. Rotation of lock ring 1407 causes slide 1409 to move from a first position, where a first address is displayed on shipping label 1008, to a second position, where a second address is displayed on shipping label 1008. Electronic lock sensor 1403 determines and communicates the lock/unlock status of transport carton lid 1009.

Figure 11:
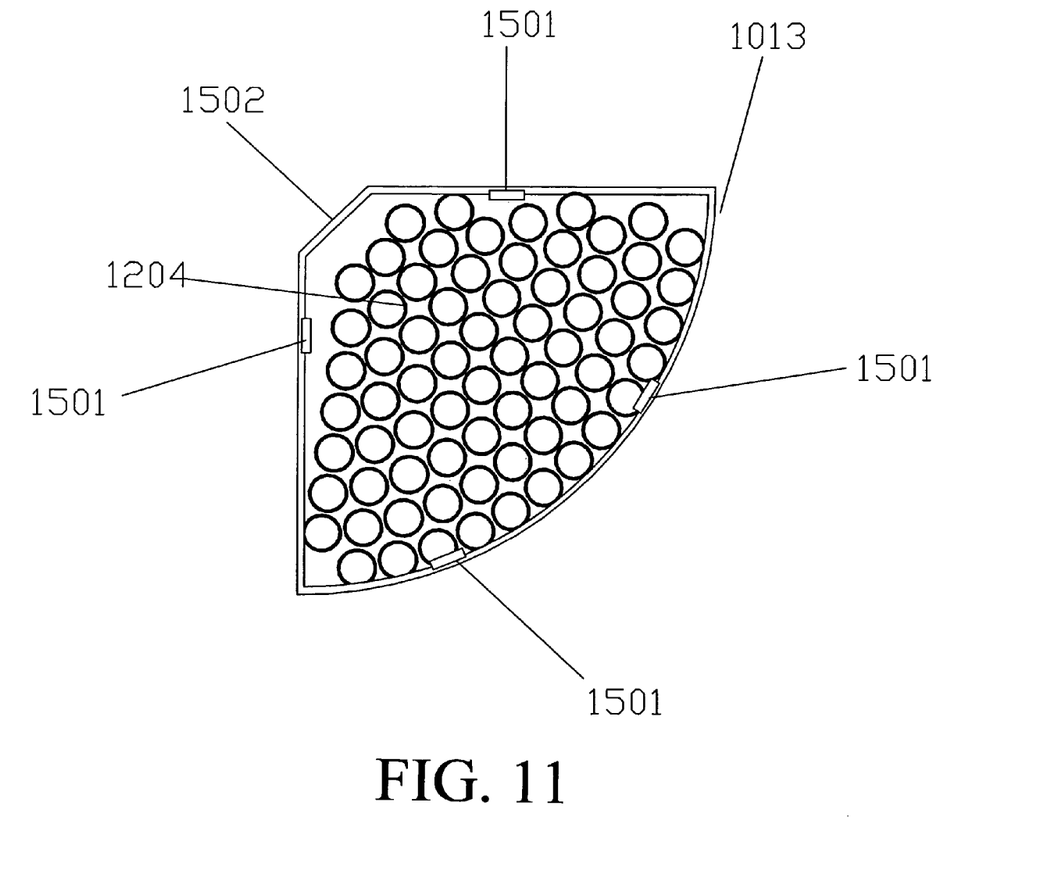
FIG. 11 is a plan view of an embodiment of the transport container base of the present invention.

Referring to FIG. 11, a top view of transport carton base 1013 is shown. Sliding lock receivers 1501 extend from and are spaced around the periphery of transport carton base 1013. Sliding lock receivers 1501 are positioned to receive lock arms 1408 (not shown). Side walls of base 1013 create a volume into which bottles of product 1204 are stored.

In this embodiment, data/power port 1004 contains nine configurable contact points. These contact points are randomly configurable for either power or data functionality. Transport carton 1007 further includes an RFID tag (not shown). This tag is affixed at the repackaging pharmacy and programmed with a unique serial number. When a transport carton 1007 is placed in proximity to an RDS 12 prior to loading into the RDS, RFID reader 118 queries the transport carton 1007 for this unique serial number. The RDS then compares the received serial number to its database to determine if that particularly transport carton 1007 is expected and authorized for loading into vault 100 inventory. If this verification is not successfully completed, loading into the RDS is prevented.

Transport carton 1007 also includes internal sensors (not shown) that measure and record environmental conditions (temperature and humidity) and physical conditions (container orientation and acceleration). These sensors input data to a microprocessor and memory which communicate with the RDS through power/data port 1004. Additionally, the open/close history and status of transport carton 1007 and the transit time are recorded and communicated to the RDS.

Figure 9:
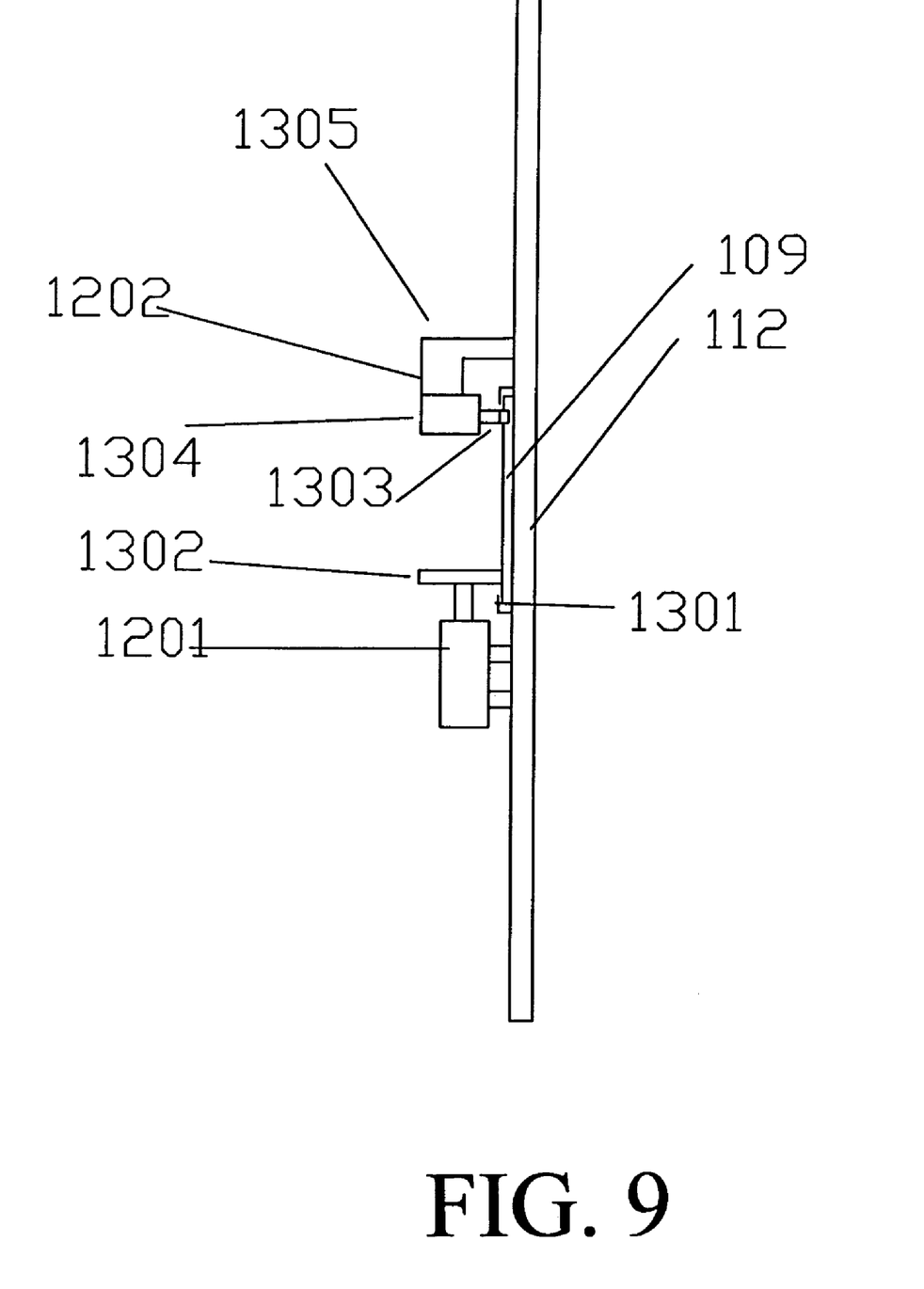
FIG. 9 is an side view of an embodiment of the loading door locking system of the present invention.

Referring to FIG. 9, the locking mechanism for loading door 109 is shown. Loading door 109 is positioned interior to vault 100, proximate to vault door 112. Loading door 109 is supported by door guides 1301 which are channel shaped rails in which loading door 109 slides and which are attached to vault door 112. Movement of loading door 109 is effected by motor 1201 which drives drive wheel 1302 which frictionally engages loading door 109 and causes it to slide in guide rails 1301. Loading door lock 1202 is attached to support 1305 and consists of solenoid 1304 and lock pin 1303. Energizing/de-energizing solenoid 1304 causes lock pin 1303 to extend/retract. Loading door 109 further includes a bore for receiving lock pin 1303 when lock pin 1303 is in its extended, or locked, position. Loading door 109 is equipped with position sensing hardware and software which includes limit sensors, amperage detection, optical sensors and in some embodiments encoders.

Vault Loading and Inventory Control System

A proprietary software application running on RDS computer 205 controls the loading of product 1204 from a transport carton 1007 to vault 100 storage area. Storage is provided via a high density design that allows for maximum utilization of available storage space. In one embodiment, as seen in FIG. 4, a plurality of rotating shelves 602 are stacked vertically about a central support and axel 908. Each tray has an access slot 603 that runs from the circumference of the tray to the central axis of the tray and that is sufficiently wide to allow movement of horizontal arm 414 and grabber carriage 1100 within slot 603. Slots 603 are vertically alignable so that horizontal arm 414 may be raised completely through the entire stack of trays. In this embodiment, the grabber assembly 1100 travels linearly between vertical arm 415 and shelve axel 904. Rotation of a shelve 602 under grabber assembly 1100 allows all storage locations on each shelve 602 to be accessible by grabber assembly 1100. In another embodiment, square or rectangular trays are utilized in conjunction with an elevator system that moves trays as necessary to allow access, between the trays, for the robotic arm system.

Figure 7:
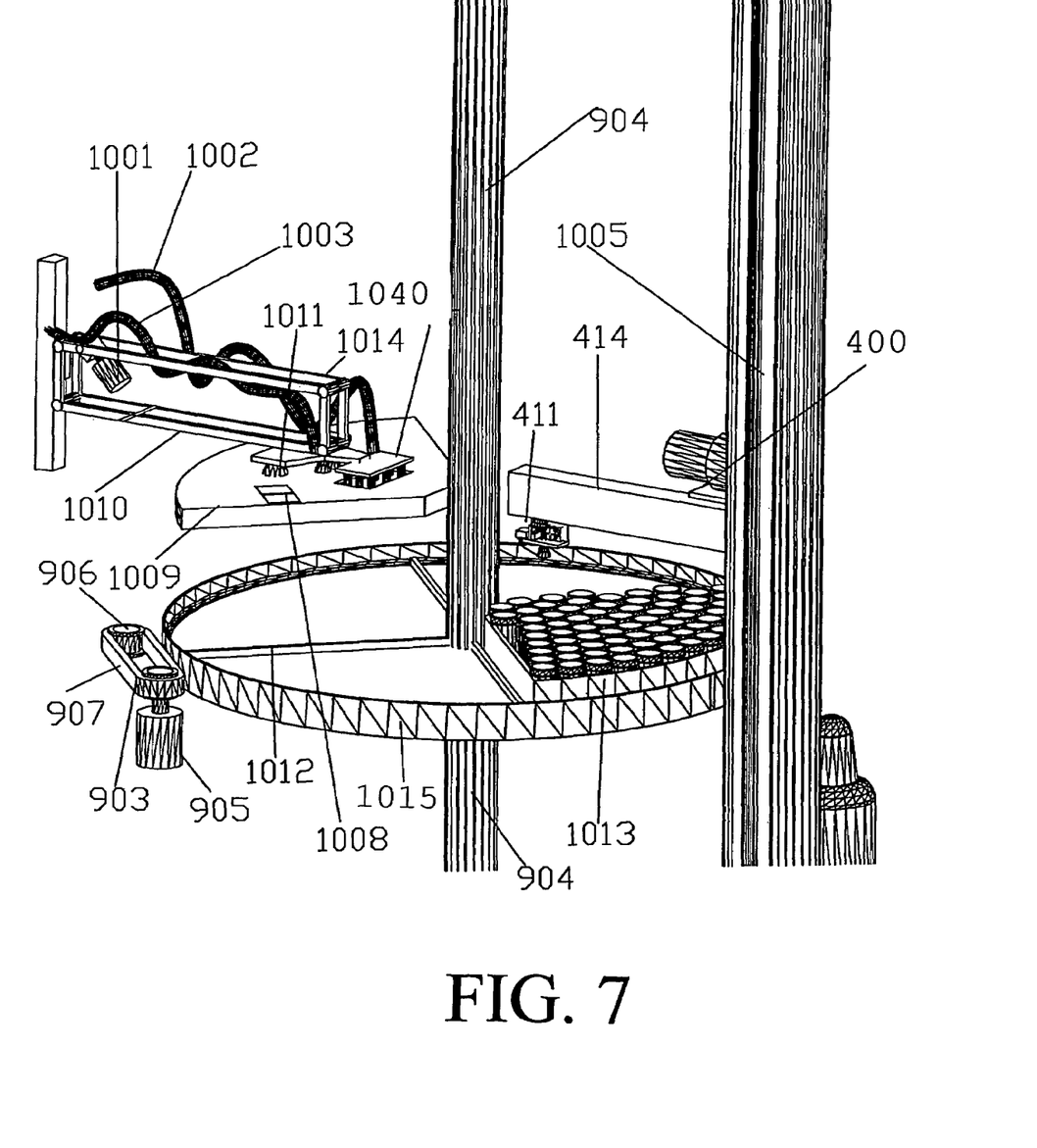
FIG. 7 is an isometric view of the loading system of an embodiment of the present invention.

Referring to FIG. 7, product 1204 receiving and unloading is shown. Transport carton 1007 has been loaded into product receiving tray 1015 through loading door 109 (not shown). Transport carton lid 1009 is shown after being unlocked and removed from transport carton base 1013 by lid lifting system 1010 and with product receiving tray 1015 rotated 180 degrees. Lid lifting system 1010 includes arm 1014, lid lifting motor 1001, data/power cable 1002, vacuum supply line 1003, data/power contact 1004, and suction cups 1011. Upon loading of a transport carton 1007 into vault 100, lifting motor 1001 positions lid lifting system 1010 to engage lid 1009. Data/power contact 1040 engages data port 1004 on lid 1009. Data related to the content of the transport carton 1007, and environmental parameters to which the transport carton 1007 has been exposed during shipment are downloaded to CPU 205 and verified and quality checked. If all checks are successful, transport carton locking mechanism 1402 (not shown) is provided power and lock arms 1408 (not shown) are moved to their unlocked position. Vacuum line 1003 then supplies a vacuum to suction cups 1011 and lift lifting motor 1001 lifts transport carton lid 1009 to the position shown. Drive system 903 is then engaged to rotate product receiving tray 1015 into unloading position under robotic arm system 400. If one or more quality checks are out of tolerance, no product loading occurs and the RDS transmits an appropriate message to the repackaging pharmacy.

During the unloading process, each individual product container is removed from the transport carton 1007 by the robotic arm system 400. Each product container is lifted from the transport carton by the grabber assembly suction cup 412. Each individual product container is shipped from repackaging pharmacy 17 with a bar code label that identifies the content of the container and may also include an RFID tag that provides a second identification of container contents.

The product container's label and RFID tag are then read with a bar code scanner and RFID system (not shown) to determine the contents of the container and the pedigree, e.g., the manufacturer, repackager, lot number, expiration date, of the product within the container and stored in memory. In addition other forms of product identification may be used including but not limited to height, width, shape and weight. The RDS computer 205 directs the robot arm assembly to move the container to a specified location on a rotating shelve 602 in the vault 100. Each rotating shelve has a plurality of receiving locations, each defined by specific Cartesian (x-y-z) coordinates. For example, if the RDS computer 205 directs that a bottle of product 1204 be placed in the lowermost rotating shelve 602, robotic arm system 400 moves the bottle vertically until the bottle is at a y-coordinate (vertical) position just above that rotating shelve 602. Drive system 903 for that rotating shelve 602 then rotates the shelf to the specified rotational position. Robotic arm system 400 then moves the bottle horizontally to the specified position in the x-y plane.

Once the bottle is positioned in the specified position, and the rotating shelve 602 is in the specified rotational position, vacuum is stopped and the bottle is released by grabber suction 412. The RDS computer 205 stores the exact position and content of the container in an inventory database. This process is repeated until all product 1204 containers have been removed from the transport carton 1007 and placed in one of the rotating shelves 602 and the inventory database has been populated. In the event that non-prescription medications are to be loaded into inventory, some or all of the product verification steps can be eliminated.

Product Dispensing Verification

Prior to dispensing product 1204 to a user, multiple, independent verifications are performed by the RDS to ensure that the correct type and quantity of product are dispensed. After a container of product 1204 is removed from a rotating shelve 602, robotic arm system 400 moves the container through a series of verification processes. These verifications include a barcode scan, verification of the container shape and size by movement past sensors, bitmap photographic recognition and optical character recognition software, verification of the container weight via an accelerometer or scale, visual verification through direct imaging, and/or receipt of RFID information from the product container. The shape of the container and the height of the container may also be verified to ensure that the proper product is being dispensed. The RDS software is programmable to require that one or all of these verifications is to be successfully completed before a product 1204 is dispensed to a user. This verification process is critical to ensuring that only the correct product 1204 is dispensed to a user.

Product Dispensing Labeling

Products are received from the repackaging pharmacy 17 with the repackaging pharmacy's label and RFID tag on the product container. After a container of product 1204 has completed the verification process, a patient specific label is printed and applied to the container. The RDS labeling system is comprised of software that resides on the RDS computer 205, a label printer, and a label applicator. In one embodiment, the label printer and label applicator are positioned in the base of the vault 100. Robotic arm system 400 moves a container of product to be dispensed into position for labeling to occur. Once the product has been labeled a bitmap image of the applied label is recorded and stored in a designated database.

RDS Operation

In one embodiment, a person who desires to obtain prescription medication from an RDS must first complete the PRS registration process and supply the necessary personal, medical, and biometric information. Alternatively, identification can be verified through the use of a credit card or smart card, or other device upon which data can be stored and then read at the RDS. Once registered, such a person may obtain an electronic prescription from a participating prescription provider. The electronic prescription is communicated over a communications network to the RDS which may be located at the provider's office, at a pharmacy, or at another remote location. Once the prescription is communicated, the prescription is then available to be received at the RDS by the patient.

At the RDS, the patient must first enter his/her personal biometric information through biometric reader 114. The RDS then compares the biometric information entered with the biometric information database compiled through the PRS system. Once a patient's identity is verified, the RDS computer system determines the prescription or prescriptions authorized to be dispensed to the patient. For each such prescription, the RDS communicates through the PBMS 15 to verify insurance coverage and to determine the amount of co-pay, or other payment, that is required. The patient then provides payment information which is verified through the FTS 14, or pays directly through cash receiver 122. Once payment is confirmed, the RDS printer 121 prints a financial receipt and a prescription information sheet and begins the dispense sequence.

The RDS computer 205 consults the inventory database to determine the storage location of the product 1204 to be dispensed. Robotic arm system 400 then retrieves the product 1204 from the applicable rotating shelve 602. The product 1204 is then moved by robotic arm system 400 into position for product verification. One or more verifications consisting of barcode scan, RFID tag reading, container shape and size, bitmap imaging and OCR character recognition, container weight are performed. If the selected product 1204 does not match the product prescribed, the product 1204 is returned by robotic arm system 400 to transport carton 1007 and the RDS computer identifies the next storage location where appropriate product 1204 is stored.

If the verification process is successfully completely, the product 1204 is moved to the product labeling area inside vault 100. There, a patient specific label, containing, a bar code, the patient's name, prescription number, and directions for taking the medication is printed and applied to the product 1204. Once this patient specific label is printed and applied, a second verification process ensues. This second verification includes a bar code scan and the creation of a bitmap image of the label. The bitmap image is compared, via OCR software, to the image stored in the RDS computer for that particular prescription. Upon completion of this second verification, product 1204 is moved by robotic arm system 400 to the product dispensing area and dispensed through dispensing slot 105. Prescription pick-up sensor 105 provides a signal to RDS computer 205 that the prescription has been removed from dispensing slot 105 and completes the dispensing process. In the event that a dispensed product is not removed from dispensing slot 105 within a selectable time frame, the product is automatically retrieved from the dispensing slot and removed from inventory.

In another embodiment, the RDS can also dispense product 1204 to patients that have received a paper prescription instead of an electronic prescription from the provider. In this embodiment, the patient, after verifying identity at the RDS, inserts the paper prescription into prescription reader 117. The prescription is scanned and a bitmap image is generated and transferred via the communications network to a participating pharmacist. This pharmacist then reads the prescription and converts it into an electronic prescription which is communicated back to the RDS. At this point, the dispensing process proceeds as described above.

In yet another embodiment, the RDS can also dispense non-prescription products to patients that have not previously completed the PRS 10 process. In this embodiment, non-prescription products are also stocked in the RDS. These products are available to persons without the requirements that a prescription be first transmitted to the RDS and that the user supply biometric identification prior to receiving product.

I claim:

1. A method for providing high density storage of, and random access to, prescription medications for dispensing through a remote dispensing system comprising the steps of:
   a. providing a remote dispensing system with a vault for storing said prescription medications;
   b. providing a plurality of shelves within said vault, each of said shelves connected to, and rotatable about, a central support axel;
   c. providing a plurality of receiving spaces for storing said prescription medication on each shelve;
   d. assigning a unique location coordinate for each of said receiving spaces on each of said shelves;
   e. stocking said receiving spaces with said prescription medications;
   f. creating a database containing the location coordinate for each of said prescription medications;
   g. providing a slot in each of said shelves, said slots alignable to create a vertical passage through all of said shelves;
   h. providing a robotic arm within said vault, said robotic arm capable of vertical movement through said vertical passage and horizontal movement within said slots;
   i. providing a computer to operate said robotic arm and to manage said database;
   j. whereby, each of said receiving spaces may be randomly accessed by said robotic arm by aligning said slots, moving said robotic arm vertically to a first position immediately above the shelve to be accessed, rotating said shelve to be accessed under said robotic arm, and moving said robotic arm horizontally to a specified receiving space.

2. A method for stocking an automatic dispensing machine comprising the steps of:
   a. providing an automatic dispensing machine;
   b. providing a [lockable] transport carton containing a plurality of individual products to be stocked;
   c. inserting said transport carton into said automatic dispensing machine;
   d. removing said individual products from said transport carton;
   e. placing each of said individual products in a unique storage location identifiable by Cartesian coordinates; and
   f. creating a database of said unique storage locations.

3. The method of claim 2 further including the steps of:
   a. identifying each of said individual products and creating a database of said identified products; and
   b. associating said database of said identified products with said database of unique storage locations.

* * * * *